(12) United States Patent
Fantinel et al.

(10) Patent No.: US 8,471,050 B2
(45) Date of Patent: Jun. 25, 2013

(54) ORGANOMETALLIC TRANSITION METAL COMPOUND, CATALYST SYSTEM AND PREPARATION OF POLYOLEFINS

(75) Inventors: Fabiana Fantinel, Verona (IT); Ilya Nifant'ev, Moskow (RU); Shahram Mihan, Bad Soden (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 13/381,327

(22) PCT Filed: Jul. 20, 2010

(86) PCT No.: PCT/EP2010/004436
§ 371 (c)(1),
(2), (4) Date: Feb. 23, 2012

(87) PCT Pub. No.: WO2011/012245
PCT Pub. Date: Feb. 3, 2011

(65) Prior Publication Data
US 2012/0142874 A1    Jun. 7, 2012

Related U.S. Application Data

(60) Provisional application No. 61/273,159, filed on Jul. 31, 2009.

(30) Foreign Application Priority Data

Jul. 27, 2009 (EP) .................................. 09009670

(51) Int. Cl.
C08F 4/653 (2006.01)
C08F 4/6592 (2006.01)
C08F 4/642 (2006.01)
B01J 31/22 (2006.01)

(52) U.S. Cl.
USPC ............ 556/53; 502/103; 502/113; 502/152; 502/167; 526/113; 526/114; 526/115; 526/160; 526/165; 526/169.1; 526/348; 526/943

(58) Field of Classification Search
USPC ..... 556/53; 502/103, 113, 152, 167; 526/113, 526/114, 160, 165, 169.1, 348, 943
See application file for complete search history.

(56) References Cited

U.S. PATENT DOCUMENTS

| 3,242,150 A | 3/1966 | Scoggin |
| 3,248,179 A | 4/1966 | Norwood |
| 5,420,220 A | 5/1995 | Cheruvu |
| 6,262,201 B1 | 7/2001 | Welch et al. |
| 6,417,302 B1 | 7/2002 | Bohnen |
| 2004/0249096 A1 | 12/2004 | McCullough |

FOREIGN PATENT DOCUMENTS

| EP | 1710247 | 10/2006 |
| WO | WO-9704015 | 7/1996 |
| WO | WO-9736937 | 10/1997 |
| WO | WO-99/06414 | 2/1999 |
| WO | WO-00/31090 | 6/2000 |
| WO | WO-03066699 | 8/2003 |
| WO | WO-2005/103095 | 11/2005 |
| WO | WO-2005103096 | 11/2005 |
| WO | WO-20070307836 | 4/2007 |
| WO | WO-2007101053 | 9/2007 |

*Primary Examiner* — Caixia Lu

(57) ABSTRACT

The present invention relates to non-symmetrical organometallic transition metal compounds of the compound of the formula (I)

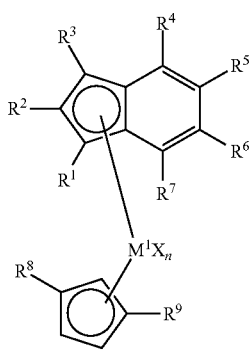

where
$R^8$ and $R^9$ are identical or different and each an substituted or unsubstituted organic radical having from 1 to 40 carbon atoms,
catalyst systems comprising at least one of the organometallic transition metal compounds of the present invention and a process for preparing polyolefins by polymerization or copolymerization of at least one olefin in the presence of one of the catalyst systems of the present invention.

12 Claims, No Drawings

ORGANOMETALLIC TRANSITION METAL COMPOUND, CATALYST SYSTEM AND PREPARATION OF POLYOLEFINS

This application is the U.S. national phase of International Application PCT/EP2010/004436, filed Jul. 20, 2010, claiming priority to European Application 09009670.2 filed Jul. 27, 2009 and the benefit under 35 U.S.C. 119(e) of U.S. Provisional Application No. 61/273,159, filed Jul. 31, 2009; the disclosures of International Application PCT/EP2010/004436, European Application 09009670.2 and U.S. Provisional Application No. 61/273,159, each as filed, are incorporated herein by reference.

FIELD OF THE INVENTION

The present invention relates to organometallic transition metal compounds. The present invention further relates to catalyst systems comprising at least one of the organometallic transition metal compounds of the present invention and a process for preparing LLDPE (linear low density polyethylene) by copolymerization of ethylene and at least one α-olefin having 3 to 12 carbon atoms in the presence of one of the catalyst systems of the present invention.

PRIOR ART

LLDPE-copolymers of ethylene with α-olefins, such as propene, 1-butene, 1-pentene, 1-hexene or 1-octene, can be prepared, for example, using classical Ziegler-Natta catalysts based on titanium or else by means of metallocenes.

In U.S. Pat. No. 5,420,220 a monomodal LLDPE is disclosed which is produced by copolymerization of ethylene and hexene with a catalytic active bis(n-butylcyclopentadienyl) zirconium dichloride in a fluidized bed reactor. The use of higher α-olefin comonomers involves the problem of reduced efficiency of comonomer incorporation, i.e. the higher the α-olefin is the lower is the comonomer incorporation.

In view of this, WO 03/066699 A1 describes a polymerization catalyzed by a single site catalyst wherein ethylene is copolymerized with at least two $C_{4-12}$ α-olefins.

WO2007/037836 A1 and WO2007/101053 A1 refer to hybrid catalyst systems using two different metallocene catalysts for the production of bimodal polyethylene. The inventions refer to metallocene-based catalyst system which can produce high molecular weight polyethylene with low levels of long chain branching and to other metallocene-based catalyst systems which are more responsive to hydrogen and produce low molecular weight polyethylene.

Thus, there continues to be a need to find new metallocene catalyst systems which can achieve an improvement in the combination of high molar mass of the copolymer and high comonomer incorporation, also when using higher α-olefins, and which are especially suitable for hybrid catalyst systems with other transition metal compounds suitable as catalysts for lower molecular weight polymers.

SUMMARY OF THE INVENTION

It is an object of the present invention to find organometallic transition metal compounds which, when used as catalyst constituents, are able to achieve a high comonomer incorporation and at the same time make it possible to provide ethylene copolymers having high molecular weights compared to the known metallocenes. Furthermore, the organometallic transition metal compounds should be able to be obtained in an economical way.

We have found that this object is achieved by organometallic transition metal compounds of the formula (I)

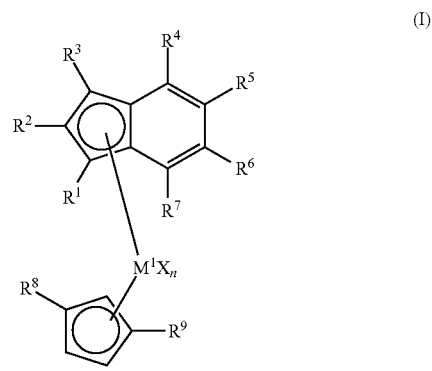

where
$M^1$ is an element of group 3, 4, 5 or 6 of the Periodic Table of the Elements or the lanthanides,
the radicals X are identical or different and are each a halogen or an organic radical having from 1 to 40 carbon atoms, with two organic radicals X also being able to be joined to one another,
n is a natural number from 1 to 4,
$R^1$, $R^2$, $R^3$, $R^4$, $R^7$ are identical or different and are each hydrogen or an organic radical having from 1 to 40 carbon atoms,
$R^5$ and $R^6$ are identical or different and are each hydrogen or an organic radical having from 1 to 40 carbon atoms or $R^5$ and $R^6$ together with the atoms connecting them form a monocyclic or polycyclic, substituted or unsubstituted ring system which has from 5 to 40 carbon atoms and may also contain heteroatoms selected from the group consisting of the elements N, O and S, in particular S and N,
$R^8$ and $R^9$ are identical or different and each an organic radical having from 3 to 40 carbon atoms.

$M^1$ is an element of group 3, 4, 5 or 6 of the Periodic Table of the Elements or the lanthanides, for example titanium, zirconium, hafnium, vanadium, niobium, tantalum, chromium, molybdenum or tungsten, preferably titanium, zirconium, hafnium. Particularly preferred is $M^1$ being zirconium or hafnium and especially zirconium.

The radicals X are identical or different, preferably identical, and are each a halogen or an organic radical having from 1 to 40 carbon atoms, with two organic radicals X also being able to be joined to one another. X is preferably $C_1$-$C_{20}$—, in particular $C_1$-$C_4$-alkyl, $C_2$-$C_{20}$—, in particular $C_2$-$C_4$-alkenyl, $C_6$-$C_{30}$—, in particular $C_6$-$C_{22}$-aryl, a $C_6$-$C_{30}$—, in particular $C_6$-$C_{22}$-arylalkyl group, —$OR^{10}$ or —$NR^{10}R^{11}$, in particular —$OR^{10}$, where two radicals X may also be joined to one another. It is also possible for two radicals X to form a substituted or unsubstituted diene ligand, in particular a 1,3-diene ligand. The radicals $R^{10}$ and $R^{11}$ are each $C_1$-$C_{10}$—, preferably $C_1$-$C_4$-alkyl, $C_6$-$C_{30}$—, preferably $C_6$-$C_{22}$-aryl, $C_6$-$C_{30}$—, preferably $C_6$-$C_{22}$-arylalkyl, $C_1$-$C_{10}$—, preferably $C_1$-$C_4$-fluoroalkyl or $C_6$-$C_{30}$—, preferably $C_6$-$C_{20}$-fluoroaryl. Also preferred is X being halogen, for example fluorine, bromine, chlorine, iodine. Most preferably X are identical and each methyl or chlorine.

The index n is a natural number from 1 to 4 which is in general equal to the oxidation number of $M^1$ minus 2. In the case of elements of group 4 of the Periodic Table of the Elements, n is 2.

$R^1$, $R^2$, $R^3$, $R^4$, $R^7$ are identical or different and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{22}$-fluoroaryl, $C_6$-$C_{40}$-arylalkyl, or a $C_2$-$C_{40}$-heteroaromatic radical containing at least one heteroatom selected from the group consisting of the elements O, N and S. $R^1$ and $R^3$ preferably are identical and are each hydrogen. $R^2$ preferably is hydrogen or a $C_1$-$C_8$-alkyl radical. $R^4$ and $R^7$ preferably are the same or different and are each selected from hydrogen, a $C_1$-$C_{10}$-alkyl, a $C_6$-$C_{40}$-aryl radical, or $C_5$-$C_{40}$-heteroaromatic radical containing at least one heteroatom selected from the group consisting of O, N, S and P. Especially preferred are $R^4$ and $R^7$ being identical and each hydrogen.

$R^5$ and $R^6$ are identical or different and are each hydrogen or an organic radical having from 1 to 40 carbon atoms, for example a cyclic, branched or unbranched $C_1$-$C_{20}$—, preferably $C_1$-$C_8$-alkyl radical, a $C_2$-$C_{20}$—, preferably $C_2$-$C_8$-alkenyl radical, a $C_6$-$C_{30}$—, preferably $C_6$-$C_{22}$-aryl radical, a $C_6$-$C_{30}$—, preferably $C_6$-$C_{22}$-arylalkyl radical, or $R^5$ and $R^6$ together with the atoms connecting them form a monocyclic or polycyclic, substituted or unsubstituted ring system which has from 5 to 40 carbon atoms and may also contain heteroatoms selected from the group consisting of the elements N, O and S, in particular S and N. Preference is given to $R^5$ and $R^6$ together forming a substituted or unsubstituted, in particular unsubstituted, propylene or propenylene group, thus together with the indenyl system forming an hydroindacenyl or indacenyl system.

$R^8$ and $R^9$ are identical or different and each an organic radical having from 3 to 40 carbon atoms. Since the steric interactions of the radicals $R^8$ and $R^9$ with the growing polymer chain are of particular importance for the polymerization behavior and the resulting properties of the polymers which can be obtained, preference is given to organometallic transition metal compounds of the formula (I) in which both radicals $R^8$ and $R^9$ are identical or different and each a $C_6$-$C_{40}$-aryl radical or $C_6$-$C_{40}$-arylalkyl or $C_3$-$C_{40}$-aliphatic radical being branched in the α-position, e.g. $C_3$-$C_{20}$—, preferably $C_3$-$C_8$-alkyl radical, a $C_3$-$C_{20}$—, preferably $C_3$-$C_8$-alkenyl radical or a $C_3$-$C_{20}$—, preferably $C_5$-$C_8$-cycloalkyl radical. Particular preference is given to organometallic transition metal compounds of the formula (I) in which the radicals $R^8$ and $R^9$ are identical, in particular compounds in which $R^8$ and $R^9$ are organic radical being an aromatic system, especially preferred phenyl.

Furthermore, the substituents according to the present invention are, unless restricted further, defined as follows:

The term "organic radical having from 1 to 40 carbon atoms"; as used in the present context refers to, for example, $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals.

The term "alkyl" as used in the present context encompasses linear or singly or multiply branched saturated hydrocarbons, which may also be cyclic. Preference is given to $C_1$-$C_{18}$-alkyl such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present context encompasses linear or singly or multiply branched hydrocarbons having at least one C—C double bond, if desired a plurality of C—C double bonds, which may be cumulated or alternating.

The term "aryl" as used in the present context refers, for example, to aromatic and fused or unfused polyaromatic hydrocarbon substituents which may be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and substituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "arylalkyl" as used in the present context refers, for example, to aryl-containing substituents whose aryl radical is linked via an alkyl chain to the remainder of the molecule. Preferred examples are benzyl, substituted benzyl, phenethyl, substituted phenethyl and the like.

Illustrative examples of novel organometallic transition metal compounds of the formula (I), which do not, however, restrict the scope of the invention, are:

1,3-diphenylcyclopentadienyl indenyl zirconium dichloride, 1,3-diisopropylcyclopentadienyl indenyl zirconium dichloride, 1,3-diphenylcyclopentadienyl indacenyl zirconium dichloride, 1,3-diisopropylcyclopentadienyl indacenyl zirconium dichloride, 1,3-dicyclopentylcyclopentadienyl indenyl zirconium dichloride, 1,3-dicyclohexylcyclopentadienyl indenyl zirconium dichloride, 1,3-di-2-butylcyclopentadienyl indenyl zirconium dichloride, 1,3-2-pentylcyclopentadienyl indenyl zirconium dichloride, 1,3-2-hexylcyclopentadienyl indenyl zirconium dichloride.

Compared to the previously known metallocenes, the novel organometallic transition metal compounds of the formula (I) give an increase in the previously achievable comonomer content during copolymerization of ethylene with a comonomer, and at the same time give a satisfactory molar mass.

The novel organometallic transition metal compounds of the formula (I) act, particularly in the presence of suitable cocatalysts, as highly active catalyst constituents for the polymerization of olefins.

In a preferred embodiment of the invention, the catalyst system comprises at least one activating compound. They are preferably used in an excess or in stoichiometric amounts based on the catalysts which they activate. In general, the molar ratio of catalyst to activating compound can be from 1:0.1 to 1:10000. Such activator compounds are uncharged, strong Lewis acids, ionic compounds having a Lewis-acid cation or an ionic compounds containing a Brönsted acid as cation in general. Further details on suitable activators of the polymerization catalysts of the present invention, especially on definition of strong, uncharged Lewis acids and Lewis acid cations, and preferred embodiments of such activators, their mode of preparation as well as particularities and the stoichiometry of their use have already been set forth in detail in WO 05/103096 A1 from the same applicant. Examples are aluminoxanes, hydroxyaluminoxanes, boranes, boroxins, boronic acids and borinic acids. Further examples of strong, uncharged Lewis acids for use as activating compounds are given in WO 03/31090 A1 and WO 05/103096 A1 incorporated hereto by reference.

Suitable activating compounds are both as an example and as a strongly preferred embodiment, compounds such as an aluminoxane, a strong uncharged Lewis acid, an ionic compound having a Lewis-acid cation or an ionic compound containing. As aluminoxanes, it is possible to use, for example, the compounds described in WO 00/31090 A1 incorporated hereto by reference. Particularly useful aluminoxanes are open-chain or cyclic aluminoxane compounds of the general formula (III) or (IV)

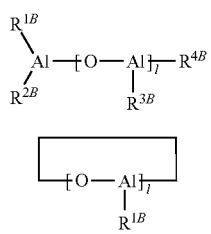

where $R^{1B}$-$R^{4B}$ are each, independently of one another, a $C_1$-$C_6$-alkyl group, preferably a methyl, ethyl, butyl or isobutyl group and I is an integer from 1 to 40, preferably from 4 to 25.

A particularly useful aluminoxane compound is methyl aluminoxane (MAO).

Furthermore modified aluminoxanes in which some of the hydrocarbon radicals have been replaced by hydrogen atoms or alkoxy, aryloxy, siloxy or amide radicals can also be used in place of the aluminoxane compounds of the formula (III) or (IV) as activating compound.

Boranes and boroxines are particularly useful as activating compound, such as trialkylborane, triarylborane or trimethylboroxine. Particular preference is given to using boranes which bear at least two perfluorinated aryl radicals. More preferably, a compound selected from the list consisting of triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane or tris(3,4,5-trifluorophenyl)borane is used, most preferably the activating compound is tris(pentafluorophenyl)borane. Particular mention is also made of borinic acids having perfluorinated aryl radicals, for example $(C_6F_5)_2BOH$. More generic definitions of suitable boron-based Lewis acids compounds that can be used as activating compounds are given WO05/103096 incorporated hereto by reference, as said above. Compounds containing anionic boron heterocycles as described in WO 97/36937 incorporated hereto by reference, such as for example dimethyl anilino borato benzenes or trityl borato benzenes, can also be used suitably as activating compounds.

Further suitable activating compounds are listed in WO 00/31090 and WO 99/06414, here incorporated by reference.

The catalytic active compound of formula (I) is especially suitable for hybrid catalyst system, comprising a second active catalytic compound. Examples of those active catalytic compounds are other early transition metal compounds or late transition metal compounds. Preferably the catalyst system comprises a compound of formula (I) and a late transition metal compound, especially an iron compound.

Especially preferred compounds are 2,6-diacetylpyridinebis(2,4-dimethylphenylimine)iron dichloride, 2,6-diacetylpyridinebis(2,4,6-trimethylphenylimine)iron dichloride, 2,6-diacetylpyridinebis(2-chloro-6-methylphenyl)iron dichloride, 2,6-diacetylpyridinebis(2,6-diisopropylphenylimine)iron dichloride, 2,6-diacetylpyridinebis(2,6-dichlorophenylimine)iron dichloride, 2,6-pyridinedicarboxaldehydebis(2,6-diisopropylphenylimine)iron dichloride.

The catalyst system may further comprise, as additional component, a metal compound as defined both by way of generic formula, its mode and stoichiometry of use and specific examples in WO 05/103096, incorporated hereto by reference. The metal compound can likewise be reacted in any order with the catalyst components (A) and (B) and optionally with the activating compound and the support.

To prepare the polyethylene of the invention, the ethylene is polymerized optionally with α-olefins having from 3 to 12 carbon atoms.

The α-olefins having from 3 to 12 carbon atoms are preferably in particular linear $C_3$-$C_{10}$-1-alkenes such as propene, 1-butene, 1-pentene, 1-hexene, 1-heptene, 1-octene, 1-decene or branched $C_3$-$C_{10}$-1-alkenes such as 4-methyl-1-pentene. Particularly preferred α-olefins are 1-butene and 1-hexene. It is also possible to polymerize mixtures of various α-olefins. Preference is given to polymerizing at least one α-olefin selected from the group consisting of ethene, propene, 1-butene, 1-pentene, 1-hexene, 1-heptene, 1-octene and 1-decene. Monomer mixtures containing at least 50 mol % of ethene are preferably used.

The polymerization can be carried out in a known manner in bulk, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are all possible. As solvent or suspension medium, it is possible to use inert hydrocarbons, for example isobutane, or else the monomers themselves.

The polymerizations are usually carried out at temperatures in the range from −60 to 350° C., preferably in the range from 20 to 300° C., and under pressures of from 0.5 to 4000 bar. The mean residence times are usually from 0.5 to 5 hours, preferably from 0.5 to 3 hours. The advantageous pressure and temperature ranges for carrying out the polymerizations usually depend on the polymerization method. In the case of high-pressure polymerization processes, which are customarily carried out at pressures of from 1000 to 4000 bar, in particular from 2000 to 3500 bar, high polymerization temperatures are generally also set. Advantageous temperature ranges for these high-pressure polymerization processes are from 200 to 320° C., in particular from 220 to 290° C. In the case of low-pressure polymerization processes, it is usual to set a temperature which is at least a few degrees below the softening temperature of the polymer. In particular, temperatures of from 50 to 180° C., preferably from 70 to 120° C., are set in these polymerization processes. In the case of suspension polymerizations, the polymerization is usually carried out in a suspension medium, preferably an inert hydrocarbon such as isobutane or mixtures of hydro-carbons or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out either batchwise, e.g. in stirring autoclaves, or continuously, e.g. in tube reactors, preferably in loop reactors. Particular preference is given to employing the Phillips PF process as described in U.S. Pat. No. 3,242,150 and U.S. Pat. No. 3,248,179. The gas-phase polymerization is generally carried out in the range from 30 to 125° C. at pressures of from 1 to 50 bar.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed mode, in which part of the circulating gas is cooled to below the dew point and is recirculated as a two-phase mixture to the reactor. Furthermore, it is possible to use a multizone reactor in which the two polymerization zones are linked to one another and the polymer is passed alternately through these two zones a number of times. The two zones can also have different polymerization conditions. Such a reactor is described, for example, in WO 97/04015.

An important application of bimodal polyethylenes is their use for producing pressure pipes for the transport of gas, drinking water and wastewater. Pressure pipes made of polyethylene are increasingly replacing metal pipes. For this type of application, it is important that the pipe has a very long operating life without aging and brittle failure having to be feared. Even small flaws or notches in a pressure pipe can grow bigger even under low pressures and lead to brittle failure, with this process being able to be accelerated by increased temperatures and/or aggressive chemicals. It is therefore extremely important to reduce the number and size of the flaws in a pipe, for example specks or "white spots" as far as at all possible.

The preparation of the polyethylene of the invention in the reactor reduces the energy consumption, requires no subsequent blending processes and makes simple control of the molecular weight distributions and the molecular weight fractions of the various polymers possible. In addition, good mixing of the polyethylene is achieved.

The invention is illustrated by the following nonlimiting examples:

EXAMPLES

Determination of the Melting Point:

The melting point $T_m$ was determined by means of a DSC measurement in accordance with ISO Standard 3146 in a first heating phase at a heating rate of 20° C. per minute to 200° C., a dynamic crystallization at a cooling rate of 20° C. per minute down to 25° C. and a second heating phase at a heating rate of 20° C. per minute back to 200° C. The melting point was then the temperature at which the curve of enthalpy versus temperature measured in the second heating phase displayed a maximum.

Gel Permeation Chromatography:

Gel permeation chromatography (GPC) was carried out at 145° C. in 1,2,4-trichlorobenzene using a Waters 150C GPC apparatus. The evaluation of the data was carried out using the software Win-GPC from HS-Entwicklungsgesellschaft für wissenschaftliche Hard- and Software mbH, Ober-Hilbersheim. The columns were calibrated by means of polypropylene standards having molar masses ranging from 100 to $10^7$ g/mol. The mass average molar mass ($M_w$) and number average molar mass ($M_n$) of the polymers were determined. The Q value is the ratio of mass average molar mass ($M_w$) to number average molar mass ($M_n$).

Determination of the Viscosity Number (I.V.):

The viscosity number was determined in an Ubbelohde viscometer PVS 1 fitted with an S 5 measuring head (both from Lauda) in decalin at 135° C. To prepare the sample, 20 mg of polymer were dissolved in 20 ml of decalin at 135° C. for 2 hours. 15 ml of the solution were placed in the viscometer and the instrument carried out a minimum of three running-out time measurements until a consistent result had been obtained. The I.V. was calculated from the running-out times by means of the relationship I.V.=$(t/t_0-1)*1/c$, where t=mean of the running-out time of the solution, $t_0$=mean of the running-out time of the solvent, c: concentration of the solution in g/ml.

Examples 1, C2, C3

Unsupported Catalyst Systems

Example 1

Preparation of Metallocene 1

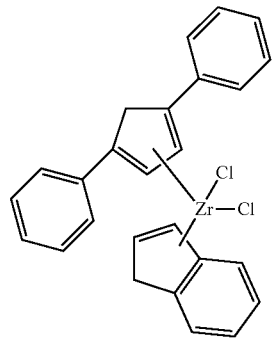

Metallocene 1: 2,5-diphenylcyclopentadienyl indenyl zirconium dichloride

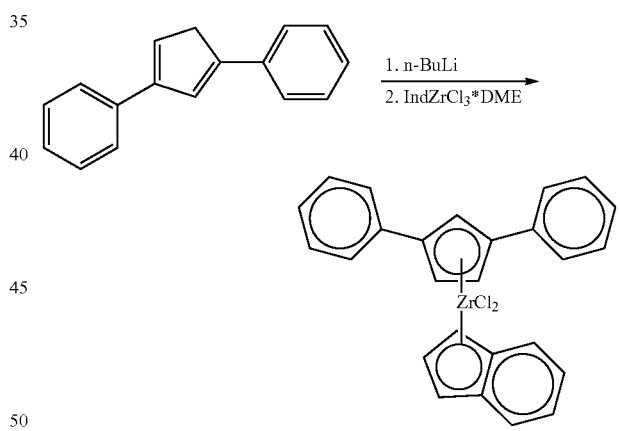

4.35 g (0.02 mol) of Ph$_2$CpH was dissolved in 255 ml of Et$_2$O. the resulting solution was cooled to −50° C. and 1.6 M n-butyllithium in hexane (12.9 ml, 0.02 mol) were added for 10 min while stirring. Subsequently, the solution was allowed to warm up to room temperature and was stirred for another 3 h at room temperature. During this time lithium salt precipitates. The obtained suspension was cooled again to −50° C. and IndZrCl$_3$*DME (12.6 g as a mixture with toluene, DME and inorganic impurities, proposing that it contains 0.023 mol of IndZrCl$_3$) was added. The resulting mixture was allowed to warm to room temperature and then was stirred overnight. Next day precipitate was filtered, washed by Et$_2$O and recrystallized from mixture n-pentane/CH$_2$Cl$_2$ in ratio 2.5/1 to give 4.5 g (45%) of pure metallocene 1 (2,5-diphenylcyclopentadienyl indenyl zirconium dichloride) as yellow powder.

NMR $^1$H (CDCl$_3$): 7.68 (d, 4H); 7.49-7.46 (group of signals, 6H); 7.36 (m, 2H); 7.21-7.18 (group of signals, 3H); 6.70 (d, 2H); 6.38 (t, 1H); 6.14 (d, 2H).

Polymerization Without Support:

Catalyst 1

11.6 mg of Metallocene 1 were solved In 300 ml toluene at 40° C. The color of solution was bright yellow. 2.5 ml MAO 30% and 3 ml hexene were added to the solution.

Polymerization

Ethylene was passed through the catalytic solution at 40° C. at ambient pressure and 1 ml hexene were added during polymerization. The temperature was controlled manually by cooling with ice bath and kept within range of target temperature +5° C. After 10 minutes the polymerization was stopped with 50 ml methanol and 30 ml HCl. After addition of 250 ml methanol the mixture was filtered and washed with methanol.

The polymer was dried at 70° C. for 4 hours. Yield was 14 g, which was 3582 kg Polyethylene/(mol Zr·h). Polymerization conditions and results are listed in Table 1 below.

Comparative Example C2

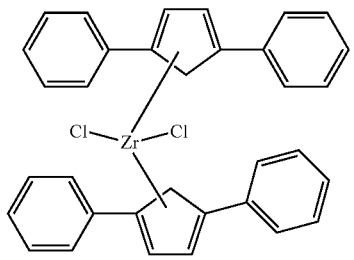

Comparative metallocene 2:
Bis(2,5-diphenylcyclopentadienyl) zirconium dichloride Comparative catalyst 2 was prepared as described in Example 1 for Catalyst 1 with the exception that instead of Metallocene 1 Comparative Metallocene 2 was used.

Polymerization

The polymerization was performed in the same way like in Example 1 with the difference that Comparative Catalyst 2 was used instead of Catalyst 1.

The polymer was dried at 70° C. for 4 hours. Yield was 5 g, which was 1013 kg PE/(mol Zr·h). Polymerization conditions and results are listed in Table 1 below.

Comparative Example C3

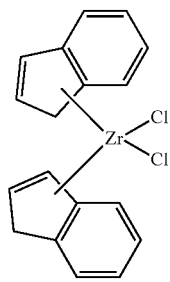

Comparative Metallocene 3: Bisindenyl Zirconium Dichloride

Comparative catalyst 3 was prepared as described in Example 1 for Catalyst 1 with the exception that instead of Metallocene 1 Comparative Metallocene 3 was used.

Polymerization

The polymerization was performed in the same way like in Example 1 with the difference that catalyst 3 was used instead of catalyst 1.

The polymer was dried at 70° C. for 4 hours. Yield was 17.3 g, which was 2563 kg Polyethylene/(mol Zr·h). Polymerization conditions and results are listed in Table 1 below.

TABLE 1

| | polymerization-unsupported catalysts | | | | | | |
|---|---|---|---|---|---|---|---|
| Example (catalyst) | Catalyst [mg] | Hexene [ml] | Yield polymer [g] | Prod. [kg PE/mol Zr*h] | IV [dl/g] | IR: total CH$_3$ [1/1000C] | IR: Hexene [%] |
| 1 (Catalyst 1) | 11.6 | 4 | 14 | 3582 | 1.93 | 20.1 | 10.8 |
| C 2 (Comparative Catalyst 2) | 10.4 | 5 | 5 | 1013 | 3.45 | 30.9 | 19 |
| C 3 (Comparative Catalyst 3) | 13.5 | 6 | 17.3 | 2563 | 2.4 | 18.7 | 9.8 |

Example 4

Supported Catalyst Systems

For the preparation of supported catalysts silica Sylopol XPO2107 from Grace calcinated at 600° C. for 6 h was used.

Example 4A

Catalyst 4:

626.1 mg of Metallocene 1 were dissolved in 26.7 ml MAO. The resulting solution was added to 21.1 g of the above calcinated XPO2107 (loading: 61.6 μmol/g) and stirred for two hours at 10° C. The obtained powder had brown-yellow color.

Polymerization in a 1.7 l autoclave:

A 1.7-l-Steelautoclave was filled under Argon with 100 g polyethylene powder having a particle size of >1 mm at 70° C. (the polyethylene powder was already dried at 80° C. for 8 hours in vacuum and stored under Argon atmosphere). 125 mg Triisobutylaluminum (TiBAl in heptane 50 mg/ml), 6.5 ml heptane as well as 50 mg Costelan AS 100 (Costelan in heptane 50 mg/ml) were added. After 5 minutes of stirring Catalyst 4 was added and the catalyst dosing unit was rinsed with 2 ml heptane. First the pressure was increased up to 10 bar at 70° C. by adding nitrogen, subsequently a pressure of 20 bar was adjusted by feeding ethylene and hexene in constant ratio to ethylene (0.1 ml/g). The pressure of 20 bar at 70° C. was kept constant for 1 hour via adding additional ethylene and hexene, fed in constant ratio to ethylene (0.1 ml/g), during polymerization. After one hour the pressure was released. The polymer was removed from the autoclave and sieved in order to remove the polymer bed.

Example 4B

Polymerization in a 240 l Autoclave:

A 240-l-Steelautoclave was filled with 240 l of Exxsol D 140/170 under nitrogen at 83° C. Subsequently, 75 mmol triethylaluminum (10.3 ml TEA 100% in 89.7 ml Exxsol) and 500 ml hexene were added at 83° C. Pressure was increased up to 8 bar at 83° C. by feeding ethylene. Then Catalyst 4 was rinsed with 70 ml Exxsol and polymerization started. During the first 10 minutes the pressure was stepwise increased to 10 bar and was kept constant for 3 hours via adding additional ethylene and hexene during polymerization. After polymerization the pressure was released. The polymer was removed from the autoclave and dried for 8 h under nitrogen.

TABLE 2 polymerization-supported catalysts

| Example (catalyst) | Catalyst [mg] | Hexene [ml] | Yield polymer [g] | Prod. [kg PE/mol Zr*h] | IV [dl/g] | IR: total $CH_3$ [1/1000C] | IR: Hexene [%] |
|---|---|---|---|---|---|---|---|
| 4A (Catalyst 4) | 179 | 17 | 138 | 771 | 1.96 | 8.1 | 4.4 |
| 4B (Catalyst 4) | 7000 | 2770 | 9500 | 1429 | 2.74 | 2.8 | 1.7 |

The new non-symmetric catalysts show a surprising high activity while still being suitable for the preparation of high molecular polyethylene having a good incorporation of a comonomer. It is remarkable that in respect to the unsupported catalyst system no drop of intrinsic viscosity can be observed.

Example 5

Hybrid Catalyst System

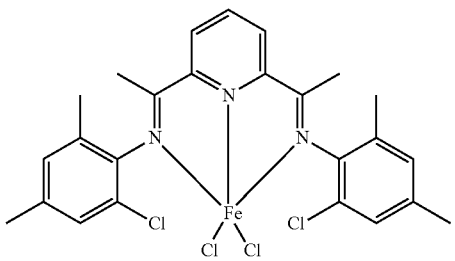

Iron Complex 5
Hybrid Catalyst 5

590 mg of metallocene 1 and 89.4 mg of Iron complex 5 were dissolved in 28.5 ml MAO. The resulting solution was added to 16.5 g of the above XPO2107 (loading: 68 μmol/g) and stirred at 10° C. for two hours. The obtained powder had lemon yellow color.

Example 5A

Polymerizations in a 1.7 l Autoclave:

A 1.7-l-Steelautoclave was filled under Argon at 70° C. with 100 g PE-powder (which was already dried at 80° C. for 8 hours in vacuum and stored under Argon atmosphere) having a particle size of >1 mm. 200 mg Isoprenylaluminum (IPRA in heptane 50 mg/ml) as well as 50 mg Costelan AS 100 (Costelan in heptane 50 mg/ml) were added. After 5 minutes of stirring catalyst was added and the catalyst dosing unit was rinsed with 7 ml heptane. First the argon pressure was increased up to 10 bar at 70° C. then a pressure of 20 bar was adjusted with ethylene. The pressure of 20 bar was kept constant for 1 hour via adding additional ethylene during the polymerization. After one hour the pressure was released. The polymer was removed from the autoclave and sieved in order to remove the polymer bed.

Example 5B

Polymerization in a 240 l Autoclave:

A 240-l-Steelautoclave was filled with 240 l of Exxsol D 140/170 from Exxon under nitrogen at 83° C. Subsequently, 75 mmol triethyalumnium (10.3 ml TEA 100% in 89.7 ml Exxsol) and 500 ml hexene were added at 83° C. First with ethylene pressure was increased up to 8 bar at 83°. Then the catalyst were rinsed with 70 ml Exxsol and polymerization started. In the first 10 minutes the pressure was stepwise increased to 10 bar and was kept constant for 3 hours via adding additional ethylene and hexene during the polymerization. After polymerization the pressure was released. The polymer was removed from the autoclave and dried for 8 h under nitrogen.

TABLE 3 polymerization-hybrid catalysts

| Example (catalyst) | catalyst [mg] | Hexene [ml] | Yield polymer [g] | Prod. [kg PE/mol Zr*h] | IV [dl/g] | IR: total $CH_3$ [1/1000C] | IR: Hexene [%] |
|---|---|---|---|---|---|---|---|
| 5A (Catalyst 5) | 179 | 15 | 115 | 590 | 1.35 | 8.5 | 5.6 |
| 5B (Catalyst 5) | 9200 | 1164 | 14000 | 1522 | 1.91 | 2.3 | 1.5 |

We claim:

1. An organometallic transition metal compound of the formula (I):

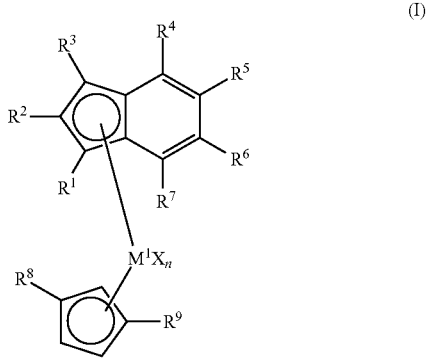

where $M^1$ is an element of group 3, 4, 5 or 6 of the Periodic Table of the Elements or the lanthanides, the radicals X are identical or different and are each a halogen or an organic radical having from 1 to 40 carbon atoms, with two organic radicals X also being able to be joined to one another, n is a natural number from 1 to 4, $R^1$, $R^2$, $R^3$, $R^4$, $R^7$ are identical or different and are each hydrogen or an organic radical having from 1 to 40 carbon atoms, $R^5$ and $R^6$ are identical or different and are each hydrogen or an organic radical having from 1 to 40 carbon atoms or $R^5$ and $R^6$ together with the atoms connecting them form a monocyclic or polycyclic, substituted or unsubstituted ring system which has from 1 to 40 carbon atoms and may also contain heteroatoms selected from the group consisting of the elements N, O and S, and $R^8$ and $R^9$ are identical or different and each are an organic radical having from 3 to 40 carbon atoms.

2. The organometallic transition metal compound of the formula (I) as claimed in claim 1 wherein $R^8$ and $R^9$ are identical or different and each are a $C_6$-$C_{40}$-aryl radical or $C_6$-$C_{40}$-arylalkyl or $C_3$-$C_{40}$-aliphatic radical branched in the α-position.

3. The organometallic transition metal compound of formula (I) as claimed in claim 1 wherein $R^8$ and $R^9$ are identical and each are a $C_6$-$C_{22}$-aryl radical.

4. The organometallic transition metal compound of the formula (I) as claimed in claim 1 wherein $M^1$ is Zr or Hf, n is 2, $R^1$, $R^3$ are each hydrogen, $R^2$ is hydrogen or a $C_1$-$C_8$-alkyl radical, $R^4$, $R^7$ are the same or different and are each selected from hydrogen, a $C_1$-$C_{10}$-alkyl, a $C_6$-$C_{40}$-aryl radical, or $C_5$-$C_{40}$-heteroaromatic radical containing at least one heteroatom selected from the group consisting of O, N, S and P, and $R^5$, $R^6$ are the same or different and are each selected from hydrogen, or $R^5$ and $R^6$ together with the atoms connecting them form a $C_5$ or $C_6$ ring system.

5. A catalyst system for the polymerization of olefins comprising at least one organic transition metal compound of formula (I) as claimed in claim 1 and at least one activating compound.

6. The catalyst system for the polymerization of olefins as claimed in claim 5, further comprising a catalytic active organic transition metal compound.

7. The catalyst system as claimed in claim 6 wherein the catalytic active organic transition metal compound is a late transition metal compound.

8. The catalyst system as claimed in claim 7 wherein the late transition metal compound is an iron compound.

9. The catalyst system as claimed in claim 5, further comprising a support.

10. A process for preparing polyolefins comprising polymerizing or copolymerizing at least one olefin in the presence of a catalyst system as claimed in claim 5.

11. The process of claim 10 wherein a copolymer is formed having a viscosity number I.V. of more than 1.9 dl/g and a hexene content of more than 5 weight % in the polymer.

12. The organometallic transition metal compound of claim 1 wherein the heteroatoms of $R^5$ and $R^6$ are selected from the group consisting of S and N.

* * * * *